United States Patent [19]

Webb, Jr.

[11] 3,966,949

[45] June 29, 1976

[54] PHARMACEUTICAL COMPOSITIONS AND PREPARING SAME

[75] Inventor: Norval Ellsworth Webb, Jr., Cincinnati, Ohio

[73] Assignee: Richardson-Merrell Inc., Wilton, Conn.

[22] Filed: Oct. 12, 1973

[21] Appl. No.: 406,013

[52] U.S. Cl. .............................. 424/250; 424/248; 424/267; 424/330

[51] Int. Cl.² ............. A61K 31/135; A61K 31/445; A61K 31/425; A61K 31/535

[58] Field of Search ........... 424/250, 172, 365, 318, 424/248, 267, 330

[56] References Cited

UNITED STATES PATENTS

| | | | |
|---|---|---|---|
| 3,652,658 | 3/1972 | Fried et al. | 424/250 |
| 3,654,277 | 4/1972 | Winter et al. | 424/250 |
| 3,663,696 | 5/1972 | Howell et al. | 424/250 |
| 3,683,084 | 8/1972 | Schmutz et al. | 424/250 |

*Primary Examiner*—Stanley J. Friedman
*Attorney, Agent, or Firm*—William J. Stein; Eugene O. Retter; George W. Rauchfuss, Jr.

[57] ABSTRACT

Water-insoluble therapeutic agents having a tertiary nitrogen capable of being protonated are stabilized and solubilized via the formation of water-soluble lipophilic liquid fatty acid salts.

10 Claims, No Drawings

PHARMACEUTICAL COMPOSITIONS AND PREPARING SAME

FIELD OF THE INVENTION

This invention relates to novel compositions of therapeutic agents which are insoluble in water having a tertiary nitrogen capable of being protonated. This invention also relates to the preparation of aqueous compositions thereof which are stable and suitable for injection.

BACKGROUND OF THE INVENTION

Standard formulations of naturally occurring medicinal agents or synthetic therapeutic agents that are insoluble in water generally involve on of two methods for the solubilization of the active ingredient. In some cases such compounds are solubilized by the judicious selection of various solvents in which the active ingredient is soluble. Alcohols, glycols, and glycerin have proven useful in dissolving and holding a large variety of insoluble compounds in solution. In other cases compounds that are either acidic or alkaline in nature are often solubilized by the formation of water-soluble salts. Alkaloids, for example, are generally formulated as their alkaloidal salts in preference to their galenical preparations since they are more stable in the form of a salt and do not precipitate on long standing.

Not infrequently acid salts of weakly basic organic therapeutic agents provide aqueous solutions which are acidic in nature and which are then unsuitable for use in parenteral compositions. Furthermore, certain therapeutic agents are less stable in acidic or weakly acidic aqueous solutions and the preparation of water-soluble and stable parenteral compositions for these compounds has been most difficult to attain. Attempts to prepare parenteral solutions for compounds of this type have previously been directed towards replacing the aqueous solvent with an oil, such as olive oil, or an alcohol, such as ethyl alcohol, glycerin, or with hydroalcoholic mixtures thereof, as for example, a 30% propylene glycol solution. Such preparations have generally proven to be unsuitable due to their hydrothermic nature on injection and due to their tendency towards irritation and necrosis. Additionally, oil injections are difficult to sterilize and have a tendency to oxidize and become rancid.

I have discovered a novel system for the preparation of solubilized and stabilized aqueous compositions of waterinsoluble therapeutic agents which are suitable for parenteral administration. More particularly my invention concerns itself with therapeutic agents which are water-insoluble and which contain a tertiary nitrogen capable of being protonated. Such compounds when reacted or complexed with an excess amount of a lipophilic, liquid fatty acid form a liquid salt which can then be solubilized in water by means of a nonionic surfactant. Solutions so obtained are characterized as micellular solutions, and are optically clear, stable, capable of sterilization and suitable for use in a variety of parenteral compositions.

SUMMARY OF THE INVENTION

This invention relates to novel therapeutic compositions comprising an effective amount of a water-insoluble therapeutic agent containing a tertiary nitrogen capable of being protonated, a lipophilic liquid fatty acid having from 14 to 24 carbon atoms, a nonionic surfactant and a pharmaceutical carrier which on addition to water provides a clear solution of the therapeutic agent. More particularly, this invention relates to clear, aqueous compositions having a pH value ranging from 6.5 to 8 which are suitable for injection.

This invention also relates to a method of preparing stabilized aqueous compositions of such water-insoluble therapeutic agents which are suitable for injection.

DETAILED DESCRIPTION OF THE INVENTION

It is well known that the solubility characteristics of a therapeutic agent are substantially altered by varying the substituents located on the molecule. Thus, the introduction of a carboxyl or a hydroxyl group generally imparts a hydrophilic character to the molecule, whereas the introduction of an alkyl group increases the lipophilic character of the molecule. Such changes, however, in addition, often drastically change the pharmacological characteristics of the molecule.

The present invention enables the solubilization and formulation in water of certain types of water-insoluble therapeutic agents heretofore not readily formulated in aqueous solutions. In general, the therapeutic agents capable of formulation in accordance with the present invention are compounds containing a tertiary nitrogen capable of being protonated. Such compounds contain a weak pair of unshared electrons which render them capable of accepting a proton and thus function as a base. When combined with a liquid, lipophilic fatty acid, they form a weak salt or a salt complex having lipophilic properties which remain in solution as an oily salt. When this water-insoluble oily salt is placed in combination with a nonionic surfactant in water, it results in a uniformly dispersed clear solution which probably exists in the form of a micellular solution. In any event, the resulting solution is optically clear, filterable, stable to heat without separation and lends itself readily to the formulation of syringeable parenteral compositions.

Two such therapeutic agents for which the instant invention is particularly useful are the compounds metiapine, 2-methyl-11-(4-methyl-1-piperazinyl)-dibenzo[b,f][1,4]-thiazepine, and clothiapine, 2-chloro-11-(4-methyl-1-piperazinyl)-dibenzo[b,f][1,4]-thiazepine. These compounds are dibenzothiazepine derivatives possessing a high level of antipsychotic activity in association with a low incidence of side effects. Both compounds are represented by the general formula:

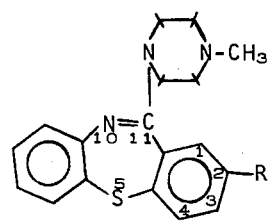

in which R is selected from the group consisting of methyl and chlorine. These compounds are quite insoluble in water but are soluble in dilute acids. Acid salts of metiapine, such as the acid tartrate, acid succinate, diglycolate, dihydrogen citrate, and the maleate salts from acidic solutions in water. Adjustment of the pH of these solutions to values above 6 results in solutions which are unstable in which the free base crystallizes and separates within a few days.

Furthermore, when such acidic 1% metiapine solutions are administered to rabbits by the intravenous route, a thrombus is formed. Acidic 2.5% metiapine solutions, administered to rabbits by intramuscular injection, result in severe necrosis and the formation of micro-thrombi. For these reasons, the administration of acidic salts of metiapine is highly undesirable.

In addition, metiapine and metiapine-like compounds undergo hydrolysis to form the more stable lactams in accordance with the following reaction scheme:

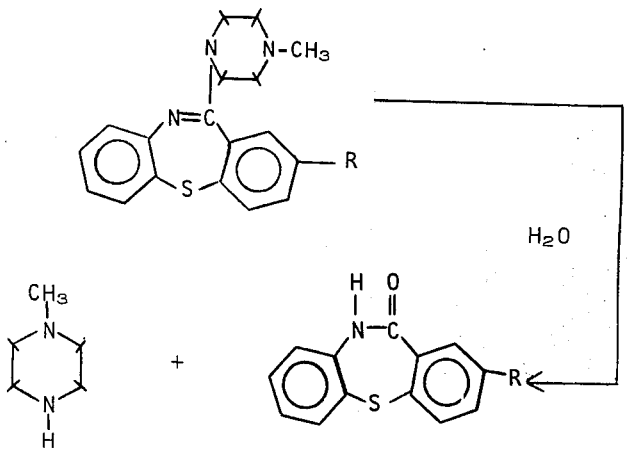

This rate of hydrolysis is increased as the acidity of the solution increases. Thus, a 10% decrease in the amount of active ingredient at 20°C. requires 1500 days at a pH of 5.06, whereas the same decrease at 20°C. at a H of 4.15 requires only 500 days.

Another therapeutic agent which is readily formulated in accordance with the present invention is the compound, α-(p-t-butylphenyl)-4-(α-hydroxy-α-phenylbenzyl)-1-piperidinebutanol. This compound is useful as an antihistamine and as an antiallergy agent and can be represented by the following structure

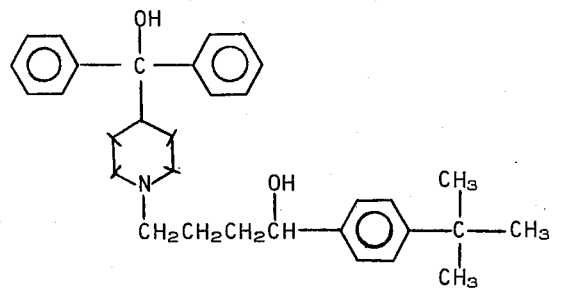

This compound is characterized by its particular insolubility in water. Nevertheless, as specifically illustrated hereinafter in Example 15, it can be formulated to a clear, elegant, aqueous solution suitable for parenteral administration.

Illustrative of a water-insoluble therapeutic agent having a heterocyclic ring which contains two different atoms is the compound, 3,4-dimethylphenyl α, cis-2,6-trimethyl-4-morpholineacetate and which has the following structural formula:

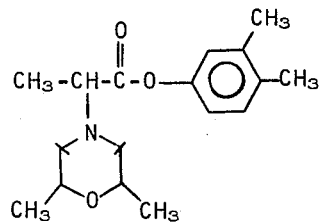

This compound, which has anesthetic properties, exhibits the same chemical, physical and irritation characteristics upon injection as observed for metiapine. A brilliantly clear formulation is obtained which remains stable at ambient temperatures as illustrated in Example 12.

To further illustrate the fact that the tertiary nitrogen need not necessarily be a ring nitrogen, a clear aqueous formulation of the water-insoluble compound 2-[p-(9-fluorenylmethyl)phenoxy]-N,N-dimethylethylamine, is prepared as illustrated in Example 13. This compound which is useful as an anti-acne agent has the following structure:

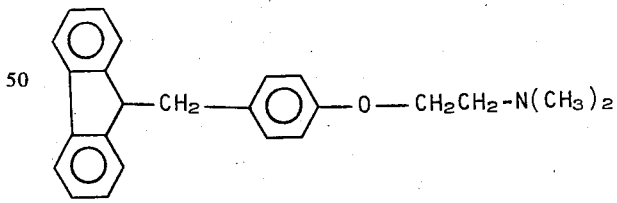

The therapeutic agents to be formulated according to the present invention are treated with a stoichiometric amount of a lipophilic liquid fatty acid. This reaction can result in the formation of either a true salt or in the formation of a salt complex or a loose salt admixture. The essential feature of this reaction is the formation of a monophasic, liquid, lipophilic salt mixture and to that end the nature of the fatty acid is critical. In the event that the particular salt so formed is insoluble in a stoichiometric amount of the lipophilic liquid fatty acid employed, an excess of acid is added to insure its solubility and the formation of a homogenous monophasic oil. Suitable acids are those which are liquid at room temperature, are lipophilic in nature and which have a high capacity to dissolve the salts which form. In general, fatty acids having a carbon content of from 14 to 24 carbon atoms and which are liquid at room temperature are suitable. Illustrative of such fatty acids are myristoleic, palmitoleic, oleic, linoleic, linolenic and isostearic acid with oleic acid being the liquid fatty acid of choice.

A nonionic surfactant is used to solubilize the water-insoluble fatty acid liquid salt. The nature of the surfactant is not critical as long as it is non-toxic in nature and remains compatible with the remainder of the formulation. Suitable surfactants include those formed by the condensation of ethylene oxide with a hydrophobic base prepared by the condensation of propylene oxide with propylene glycol, polyoxyethylated lanolin, polyoxyethylene lanolin alcohols and sorbitan fatty acid esters. The preferred surfactants employed are the polyoxyethylene sorbitan fatty acid esters, as for example, polyoxyethylene sorbitan monooleate and the polyoxyethylated vegetable oils such as those derived from corn, peanut, coconut, cottonseed and soy bean oils. The polyoxyethylated vegetable oils known as Emulphor EL-719 (Geneal Aniline and Film) which has a specific gravity (25°C.) of 1.06–1.07 and a viscosity (25°C.) of 500–800 cps, or Emulphor EL-620, which has a specific gravity (25°C.) of 1.04–1.05 and a viscosity (25°C.) of 600–1000 cps are particularly useful in carrying out the invention.

For parenteral administration, fluid unit dosage forms are prepared utilizing the water-insoluble fatty acid liquid salt, solubilized in a sterile vehicle, water being the preferred vehicle. Alternatively, isotonic solutions of saline, dextrose and mannitol can be employed. However, care must be taken in employing salts to adjust isotonicity because of the possible salting-out effect created upon the drug substance contained in the micelles. Various additional excipients can be added such as local anesthetics, buffers and preservatives to maintain sterility in multiple dose ampules. For certain therapeutic agents the addition of an anti-oxidant can be advantageously employed. The resulting parenteral solution mmay be sterilized by heat or exposure to ethylene oxide. To enhance stability, the composition can be frozen after filling into a vial and the water removed under vacuum. The lyophilized product is then sealed in the vial and an accompanying vial of water for injection is supplied to reconstitute the product immediately prior to use.

The various formulations specifically described, particularly those containing metiapine generally have an "as is" pH ranging from 6 to 7. A further advantage of the formulations described in the present invention is the fact that the resulting solutions can be adjusted with either an acid or a base over a wide pH range of from about 4 to about 8 and remain stable without precipitation. For physiological reasons, however, a pH range of 6.5 to 8.0 is preferred. Thus, the as-is pH of the aqueous formulation can be adjusted to the desired pH, with either a dilute acid, as for example, a 5% HCl solution, or with a dilute base, as for example, a 5% sodium hydroxide solution without impairing the stability of the formulation.

For oral administration either solid or fluid unit dosage forms can be prepared. In the preparation of solid compositions such as tablets, the fatty acid liquid oil salt and nonionic surfactant combination can be mixed with conventional ingredients such as talc, magnesium stearate, dicalcium phosphate, magnesium carbonate, magnesium aluninum silicate, starch, lactose, acacia, methylcellulose and functionally similar materials which act as pharmaceutical diluents or carriers. The tablets can be laminated, coated or otherwise compounded to form a dosage form affording the advantage of a prolonged or delayed action. Capsules, like tablets, are prepared by mixing the fatty acid liquid oil salt and the nonionic surfactant with an inert pharmaceutical diluent to readily enable filling the mixture into a hard gelatin capsule of appropriate size. In their simplest embodiment, the fatty acid liquid oil salt and the nonionic surfactant combination can be machine encapsulated in soft gelatin capsules per se or diluted with light liquid petrolatum or other inert oil and encapsulated in soft gelatin capsules.

The term unit dosage form as used in the specification and claims refers to physically discreet units suitable as unitary dosages for human subjects and animals, each unit containing a predetermined quantity of the active therapeutic agent calculated to produce the desired therapeutic effect in association with the required pharmaceutical diluent, carrier or vehicle. Requirements for the particular unit dosage forms prepared in accordance with the present invention are dictated by and directly dependent upon the unique characteristics of the active therapeutic agent and the particular effect which is to be achieved as well as the limitations which are inherent in the art of compounding such an active material for therapeutic use in humans and animals.

In the case of metiapine a therapeutically effective amount in humans ranges from 5 milligrams to 50 milligrams per dose. For the compound α-(p-t-butylphenyl)-4-(α-hydroxy-α-phenylbenzyl)-1-piperidinebutanol a therapeutically effective amount ranges from 2 milligrams to 25 milligrams per dosage unit form.

The following preparations are illustrative of the best mode contemplated for carrying out the present invention and are not to be construed as necessarily limiting the scope thereof.

EXAMPLE 1

| | | |
|---|---|---|
| Metiapine | 0.5 | gm |
| Oleic acid | 0.48 | gm |
| TWEEN 80, polyoxyethylene sorbitan monooleate | 6.1–9.8 | gm |
| Purified water, q.s. ad | 50.0 | ml |

The metiapine is dissolved or reacted with the oleic acid, representing a 10% excess in molar equivalency, with the aid of heat. The surfactant is added with stirring and the lipophilic liquid fatty acid salt is thoroughly mixed and homogenous. This mixture, at approximately 60°C., is diluted with stirring to approximately 50% by volume of water previously heated to 60°C. Stirring is continued for several minutes and the remainder of the water added resulting in the final volume of 50.0 ml. The mixture, which is slightly opalescent is heated with stirring to approximately 80°C. Upon cooling, the final volume is readjusted with purified water and within 3 to 24 hours aging, the mixture becomes clear having an as-is pH of 6.8.

EXAMPLE 2

| | | |
|---|---|---|
| Metiapine | 0.5 | gm |
| Oleic acid | 0.48 | gm |

| -continued | | |
|---|---|---|
| Emulphor EL-620, polyoxyethylated vegetable oil | 6.1 | gms |
| Purified water, q.s. ad | 50.0 | ml |

Following essentially the same procedure as in Example 1 but substituting the above nonionic surfactant, a clear solution was obtained.

EXAMPLE 3

| Metiapine | 0.5 | gm |
|---|---|---|
| Oleic acid | 0.48 | gm |
| Emulphor EL-719, polyoxyethylated vegetable oil | 0.6–4.9 | gms |
| Purified water, q.s. ad | 50.0 | ml |

Following essentially the same procedure as in Example 1 but substituting the above nonionic surfactant, a clear stable solution was obtained.

EXAMPLE 4

| Metiapine | 1.0 | gm |
|---|---|---|
| Oleic acid | 0.97 | gm |
| Emulphor EL-719, polyoxyethylated vegetable oil | 7.4 | gms |
| Mannitol | 3.8 | gms |
| Purified water, q.s. ad | 100.0 | ml |

Following essentially the same procedure as in Example 3, the mannitol is added and dissolved in the composition immediately prior to bringing the formulation to volume. This formulation is isotonic as determined by its freezing point depression.

EXAMPLE 5

| Metiapine | 1.0 | gm |
|---|---|---|
| Linoleic acid | 0.97 | gms |
| Emulphor EL-719, polyoxyethylated vegetable oil | 7.4 | gms |
| Purified water, q.s. ad | 100.0 | ml |

Following essentially the same procedure as in Example 3 but substituting linoleic for the oleic acid above, a clear, stable solution is obtained.

EXAMPLE 6

| Metiapine | 1.0 | gm |
|---|---|---|
| Oleic acid | 0.97 | gm |
| Emulphor EL-719, polyoxyethylated vegetable oil | 7.4 | gms |
| Dilute 5% HCl or 5% NaOH q.s ad | pH 4–8 | |
| Mannitol | 3.8 | gms |
| Purified water, q.s. ad | 100.0 | ml |

Following essentially the same procedure as in Example 4, a series of formulations are prepared having a final pH differing in unit increments ranging from a pH of 4 to 8.

EXAMPLES 7–9

| | Example 7 | | Example 8 | | Example 9 | |
|---|---|---|---|---|---|---|
| Metiapine | 5.0 | gms | 5.0 | gms | 10.0 | gms |
| Oleic acid | 4.85 | gms | 4.85 | gms | 9.7 | gms |
| Emulphor EL-719, polyoxyethylated vegetable oil | 37.0 | gms | 37.0 | gms | 37.0 | gms |
| Mannitol | 19.0 | gms | 29.0 | gms | 38.0 | gms |
| 5% NaOH q.s. ad | pH 6.6 | | "as is" | | pH 7.5 | |
| Benzyl alcohol | — | | — | | 7.5 | gms |
| Water for injection q.s. ad | 500.0 | ml | 500.0 | ml | 1000.0 | ml |

Following essentially the same procedure as in the preceding Example, benzyl alcohol is added to impart bactericidal activity to the final formulation. Its inclusion along with a slight pH adjustment prevents the appearance of slight sedimentation observed on aging. Stability studies indicate that after one year at room temperature the above formulations contain 97.8%, 98.5% and 99.8% of the original activity, respectively.

EXAMPLES 10–11

| | Example 10 | | Example 11 | |
|---|---|---|---|---|
| Metiapine | 5.0 | gms | 2.5 | gms |
| Oleic acid | 4.85 | gms | 2.42 | gms |
| Elumphor EL-719, polyoxyethylated vegetable oil | 19.0 | gms | 10.0 | gms |
| 5% NaOH solution q.s. ad | pH 7.6 | | pH 7.6 | |
| Benzyl alcohol | 0.7 | gm | 0.7 | gm |
| Water for injection q.s. ad | 100.0 | ml | 100.0 | ml |

Following essentially the same procedure as in Examples 7–9 above, the concentration of drug substance and nonionic surfactant is varied. Example 10 represents a clear thick solution containing a concentration of 50 mg of drug substance per ml.

EXAMPLE 12

| 3,4-Dimethylphenyl α,cis-2,6-trimethyl-4-morpholineacetate | 1.0 gm |
|---|---|
| Linoleic acid | 1.0 gm |
| Emulphor EL-719, polyoxyethylated vegetable oil | 7.4 gms |
| 5% NaOH solution q.s. ad | pH 7.5 |
| Water for injection, q.s. ad | 100.0 ml |

Following essentially the same procedure as in Example 5 but substituting the above therapeutic agent for metiapine, a slightly opalescent solution is obtained having an as-is pH of 5.45. A brilliantly clear formulation is obtained upon adjusting the pH to 7.5 using a 5% sodium hydroxide solution.

EXAMPLE 13

| 2-[p-(9-Fluorenylmethyl)phenoxy]-N,N-dimethylethylamine | 1.0 | gm |
|---|---|---|
| Oleic acid | 1.0 | gm |
| Emulphor EL-719, polyoxyethylated vegetable oil | 7.4 | gms |
| Benzyl alcohol | 0.72 | ml |
| Purified water, q.s ad | 100.0 | ml |

Following the same procedure as in the preceding Example, a clear solution was obtained having an as-is pH of 7.1. Maximum clarity is obtained upon the addition of a 5% sodium hydroxide solution to effect a pH 9.2.

EXAMPLE 14

| | | |
|---|---|---|
| Ergotamine base | 0.2 | gm |
| Oleic acid | 0.4 | gm |
| Emulphor EL-719, polyoxyethylated vegetable oil | 2.96 | gm |
| Benzyl alcohol | 0.75 | gm |
| Mannitol | 4.65 | gm |
| Sodium hydroxide solution, q.s. ad | pH 7.4 | |
| Water for injection, q.s. ad | 100.0 | ml |

The ergotamine base is combined with the oleic acid using a minimal amount of heat. The surfactant is added with stirring until the lipophilic liquid fatty acid salt is a homogeneous oil. Water for injection at a temperature of about 80°C. is added to approximately 58% volume, stirred to effect solution and the remaining water heated to a temperature of about 80°C. is added q.s. ad to approximate volume. The solution is cooled to room temperature and the mannitol and the benzyl alcohol added. The pH of the resulting solution is adjusted to 7.4 with a 5% sodium hydroxide solution, water added q.s. ad final folume and the solution sterilized. Each 0.1 ml of clear, isotonic solution provides 200 micrograms of ergotamine base suitable for subcutaneous or intramuscular injection.

EXAMPLE 15

Preparation of a Soft Gelatin Capsule Fill

| | |
|---|---|
| α-(p-t-Butylphenyl)-4-(α-hydroxy-α-phenylbenzyl)-1-piperidinebutanol | 5.0 gms |
| Oleic acid | 10.0 gms |
| Emulphor EL-719, polyoxyethylated vegetable oil | 60.0 gms |

The active ingredient is added to the oleic acid and heated to approximately 70°C. to effect solution and permitted to cool. The nonionic detergent is thoroughly admixed thereto and a clear oil is obtained. This composition can be used directly to liquid fill 200 soft gelatin capsules. Alternatively, 50 grams of mineral oil may be added thereto to increase the volume of the composition for ease of filling.

The above capsule fill when added to 500 ml of water provides a clear solution.

EXAMPLE 16

Preparation of a tablet formulation

One thousand tablets for oral use, each containing 25 milligrams of metiapine are prepared according to the following formulation:

| | | |
|---|---|---|
| Metiapine | 25.0 | gms |
| Oleic acid | 24.0 | gms |
| Emulphor EL-719, polyoxyethylated vegetable oil | 100.0 | gms |
| Magnesium carbonate | 50.0 | gms |
| Dicalcium phosphate | 200.0 | gms |
| Methylcellulose, U.S.P. (15 cps) | 6.5 | gms |
| Talc | 50.0 | gms |
| Calcium stearate | 2.5 | gms |

The metiapine is added to the oleic acid and warmed to about 70°C. to effect solution. The nonionic surfactant is added with stirring and a clear oil is obtained. This oil is adsorbed upon the dicalcium phosphate and magnesium carbonate, mixed well, granulated with a 0.5% aqueous solution of methylcellulose, passed through a No. 8 screen and carefully dried. The dried granules are passed through a No. 12 screen, blended with the talc and calcium stearate and compressed into tablets.

The above tablet when added to 200 ml of water provides a clear solution containing the active ingredient after sedimentation of the inert excipients.

I claim:

1. A method of preparing a stabilized aqueous parenteral composition of a water-insoluble therapeutic agent containing a tertiary amine capable of being protonated which comprises reacting said therapeutic agent with at least a stabilizing amount of a lipophilic liquid fatty acid having from 14 to 24 carbon atoms to form a lipophilic, fatty acid liquid salt; incorporating a nonionic surfactant with said liquid salt; and incorporating water to effect a solution suitable for injection.

2. A pharmaceutical composition which forms a clear solution when added to water, prepared by treating a water-insoluble therapeutic agent containing a tertiary amine capable of being protonated, with a lipophilic fatty acid which is liquid at room temperature and contains from 14 to 24 carbon atoms in a weight to weight ratio of about one part of said therapeutic agent to one part of said fatty acid and not more than one part of said therapeutic agent to two parts of said fatty acid, to form a homogenous, monophasic oil; and incorporating a nonionic surfactant in an amount sufficient to solubilize said oil when combined with an aqueous vehicle.

3. A composition according to claim 2 wherein the water-insoluble therapeutic agent is a compound having the formula:

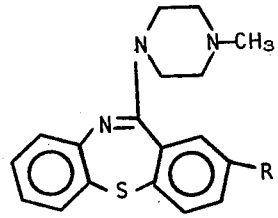

in which R is selected from the group consisting of methyl and chlorine.

4. A composition according to claim 2 wherein said water-insoluble therapeutic agent is α-(p-t-butyl-phenyl)-4-(α-hydroxy-α-phenylbenzyl)-1-piperidinebutanol.

5. A composition according to claim 2 wherein said nonionic surfactant is selected from the group consisting of the condensation products of ethylene oxide with a hydrophobic base prepared by the condensation of propylene oxide with propylene glycol, polyoxyethylated lanolin, polyoxyethylene lanolin alcohols, sorbitan fatty acid esters and polyoxyethylated vegetable oils.

6. A composition according to claim 2 wherein the lipophilic fatty acid is oleic acid and the nonionic surfactant is a polyoxyethylated vegetable oil.

7. A pharmaceutical composition which forms a clear solution when added to water, comprising a homogenous monophasic oil formed by the reaction of a water-insoluble therapeutic agent having a tertiary amine capable of being protonated with at least a stabilizing amount of a lipophilic fatty acid which is liquid at room temperature and contains from 14 to 24 carbon atoms; a pharmaceutical carrier; and a nontoxic nonionic surfactant selected from the group consisting of the condensation products of ethylene oxide with a hydrophobic base prepared by the condensation of propylene oxide with propylene glycol, polyoxyethylated lanolin, polyoxyethylene lanolin alcohols, sorbitan fatty acid esters and polyoxyethylated vegetable oils in an amount sufficient to solubilize said oil in said carriers.

8. A pharmaceutical composition according to claim 7 wherein the water-insoluble therapeutic agent is a compound having the formula:

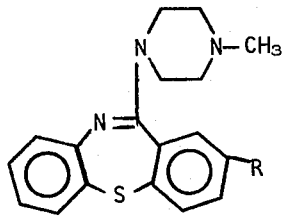

in which R is selected from the group consisting of methyl and chlorine.

9. A pharmaceutical composition according to claim 7 wherein the water-insoluble therapeutic agent is α-(p-t-butylphenyl)-4-(α-hydroxy-α-phenylbenzyl)-1-piperidinebutanol.

10. A pharmaceutical composition according to claim 7 wherein the lipophilic fatty acid is oleic acid and the nonionic surfactant is a polyoxyethylated vegetable oil.

* * * * *